United States Patent [19]

Vartuli et al.

[11] 4,273,677

[45] Jun. 16, 1981

[54] PREPARATION OF THALLIUM PROMOTED VO(PO₃)₂ OXIDATION CATALYST

[75] Inventors: James C. Vartuli, West Chester, Pa.; Lee R. Zehner, Dublin, Ohio

[73] Assignee: Atlantic Richfield Company, Los Angeles, Calif.

[21] Appl. No.: 105,367

[22] Filed: Dec. 19, 1979

[51] Int. Cl.³ .................... B01J 27/14; B01J 31/02
[52] U.S. Cl. .................................. 252/435; 252/430
[58] Field of Search ........................... 252/430, 435

[56] References Cited

U.S. PATENT DOCUMENTS

| | | | |
|---|---|---|---|
| 3,870,655 | 3/1975 | Nanba et al. | 252/435 |
| 3,907,835 | 9/1975 | Kobylinski et al. | 252/437 X |
| 3,985,775 | 10/1976 | Harrison | 252/435 X |

FOREIGN PATENT DOCUMENTS 1511479  5/1978  United Kingdom .................. 252/435

*Primary Examiner*—Delbert E. Gantz
*Assistant Examiner*—William G. Wright
*Attorney, Agent, or Firm*—Delbert E. McCaslin

[57] ABSTRACT

A method for the preparation of a thallium promoted single phase vanadium(IV)bis(metaphosphate) catalyst useful for the vapor phase oxidation of linear C₄ unsaturated olefins to prepare maleic anhydride.

14 Claims, No Drawings

4,273,677

PREPARATION OF THALLIUM PROMOTED VO(PO$_3$)$_2$ OXIDATION CATALYST

BACKGROUND OF THE INVENTION

This invention is directed to a novel method for the preparation of a thallium promoted single phase crystalline vanadium(IV)bis(metaphosphate) catalyst which provides good yields of and selectivities to maleic anhydride by the oxidation of unsaturated aliphatic hydrocarbons.

Prior art processes are known for the preparation of phosphorus-vanadium-oxygen catalyst systems which include other metals or metal compounds as potential yield improving co-catalysts such as molybdenum, copper and uranium oxides or other oxides incorporated into the catalyst system during preparation. These catalyst systems however, as well as other catalysts showing some activity for the production of maleic anhydride have generally proven to be unsatisfactory for commercial application and leave a lot to be desired since the yield and selectivity to maleic anhydride is usually low.

Phosphorus-vanadium-oxygen catalysts are usually prepared by reducing vanadium pentoxide to vanadium(IV) in water or an organic solvent with a suitable reducing acid or agent. A source of phosphorus, usually phosphoric acid, is mixed with the vanadium solution to produce a catalyst precursor which is heated to give the production catalyst. Co-catalysts are usually incorporated into the catalyst system during the solution stage of preparation and by such process there is a risk of also reducing the co-catalyst or added metal compound.

U.S. Pat. No. 3,907,835 discloses the preparation of a catalyst comprising an admixture of vanadium, uranium, phosphorus and oxygen for the gas phase preparation of maleic anhydride.

U.S. Pat. No. 3,904,652 describes a solution or "reflux" method for the preparation of a phosphorus-vanadium-oxygen complex catalyst containing one or more activators selected from zinc, copper, bismuth or lithium intimately combined therewith.

U.S. Pat. No. 3,366,648 describes a solution method employing reducing agents to form a vanadium-phosphorus catalyst complex along with a phosphorus stabilizer of an alkali metal (Group 1a metal) compound useful for the preparation of maleic anhydride.

There is no known prior art which describes the preparation of a thallium promoted crystalline VO(PO$_3$)$_2$ hydrocarbon oxidation catalyst employing a liquid phase reaction of vanadyl sulfate, thallium oxide, acetic anhydride and phosphorus pentoxide followed by a thermal treatment with the liberation of gases to form a catalyst precursor.

SUMMARY OF THE INVENTION

This invention relates to a novel method for the preparation of a thallium promoted single phase crystalline vanadium(IV)bis(metaphosphate) catalyst with improved catalytic activity for an air or oxygen partial oxidation of an unsaturated aliphatic hydrocarbon selected from 1-butene, 2-butene and 1,3-butadiene or mixtures thereof at temperatures of from about 300° C. to 600° C. by contacting the hydrocarbon and air or oxygen with the thallium promoted vanadium(IV)bis(metaphosphate) catalyst at contact times of from about 0.2 to 5 seconds of reactant feed over the catalyst, prepared by the instant method.

It is a primary object of this invention to provide a novel method for the preparation of a thallium promoted single phase crystalline vanadium(IV)bis(metaphosphate) catalyst useful as an oxidation catalyst to produce maleic anhydride.

It is another object of this invention to provide a novel method of adding thallium, in the form of thallic oxide, to a vanadium-phosphorus-oxygen catalyst system and thus ultimately forming, apparently by some chemical interaction and not by mere physical admixture, a thallium promoted VO(PO$_3$)$_2$ oxidation catalyst having intrinsic surface areas of from about 5 to 25 m$^2$/g. or higher.

These and other objects and advantages of this invention will become apparent from the description of the invention which follows and from the claims.

DESCRIPTION OF THE INVENTION

In accordance with the present invention, a thallium promoted single phase crystalline vanadium(IV)bis(metaphosphate) VO(PO$_3$)$_2$ compound is prepared by a novel method which, in addition to providing a thallium containing catalyst useful as an oxidation catalyst, also improves the intrinsic surface area of such catalyst as compared to known crystalline VO(PO$_3$)$_2$ catalyst preparation methods shown for example in U.S. Pat. No. 4,165,299.

The instant method for the preparation of the novel improved thallium promoted single phase crystalline oxidation catalyst involves a liquid phase interaction between vanadyl sulfate (VOSO$_4$), thallic oxide (Tl$_2$O$_3$), acetic anhydride and phosphorus pentoxide forming a slurry with the liberation of exothermic heat. Excess liquid is generally decanted from the resulting slurry which is then subjected to a thermal treatment for a period sufficient for the liberation of gases and the forming of a thallium-phosphorus-vanadium reaction product. The undecanted slurry may per se be subjected to thermal teratment with the acetic anhydride being vaporized off along with the gases. Stoichiometric amounts of vanadyl sulfate and phosphorus pentoxide are generally employed in preparing the thallium promoted VO(PO$_3$)$_2$ compound but excess amounts may also be employed and the excess residue removed, by water washing, after reaction, to form the catalyst precursor. The molar ratio of thallium to vanadium which is employed in the form of thallic oxide and vanadyl sulfate will generally be in the range of from about 1:10 to about 1:150 preferably 1:90 although larger or smaller amounts can be employed. The amount of acetic anhydride employed in the process can range from about 1 to 4 moles preferably 2 to 3 moles per mole of the combined vanadyl sulfate, phosphorus pentoxide and thallic oxide present. Greater amounts of acetic anhydride may be used but generally are not required.

The liquid phase reaction is generally carried out at ambient temperatures, e.g., 20° C. to 25° C. although higher or lower temperatures may be used. The thermal treatment of the slurry mixture will proceed at temperature of at least 325° C. and temperatures as high as 475° C. or higher may be used to liberate the reaction gases. It is generally preferred to carry out the thermal treatment at a temperature of between about 400° C. and 460° C. to obtain a convenient rate of reaction.

After preparation and water washing, the thallium promoted VO(PO$_3$)$_2$ compound is generally dried at 120° C., calcined in air at temperatures between about 450° C. and 500° C. or higher for at least two hours, then broken up and sieved to the appropriate Tyler Standard Sieve mesh size, usually for fixed bed reactor use. The resulting thallium promoted $VO(PO_3)_2$ compound (catalyst precursor) which has a surface area of approximately 5.0 to 25.0 $m^2/g$. requires a period of activation or conditioning for use in oxidizing the above indicated unsaturated aliphatic hydrocarbons. For the activation or conditioning the thallium-vanadium-phosphorus-oxygen catalyst precursor is subjected to temperatures which are at or above the hydrocarbon oxidation reaction temperatures which are from about 300° C. to 600° C. preferably from 450° C. to 550° C. under a flow of from about 0.2 volume percent to about 2.0 volume percent preferably 0.5 to 1.5 volume percent in air of said hydrocarbon or mixture of hydrocarbons, to be oxidized and at an apparent contact time of from about 0.5 to 3.0 seconds, preferably 0.75 to 1.5 seconds for an appropriate period, to enable the hydrocarbon conversion to reach 90 percent or more, with subsequent temperature and flow rate adjustments to desired oxidation reaction conditions. Water vapor (steam) e.g., from about 10 to 35 mole percent may be added to the reactant hydrocarbon gases during the activation period and subsequent oxidation reaction. The length of time required for activation or conditioning of the catalyst precursor and to permit the catalyst performance to become stabilized depends on the temperature employed and contact time of the hydrocarbon-air mixture but generally will be from about 4 to 8 hours. Apparent contact time calculated in seconds is equal to the flow rate of the hydrocarbon-air feed mixture at cc/second per cc of catalyst measured at ambient conditions. Once activated the thallium promoted $VO(PO_3)_2$ exhibits excellent performance as a catalyst for the oxidation of 1-butene, 2-butene and 1,3-butadiene, or mixtures thereof, to maleic anhydride for extended periods of time.

The thallium promoted $VO(PO_3)_2$ catalyst of this invention may also be prepared in the presence of a suitable carrier such as silica gel, aluminosilicates, alumina, silicon carbide and carbon to provide a support for the catalyst and thus a surface which gives physical strength and stability to the catalyst material as well as a surface area which may be up to 100 $m^2/g$. on the support. The support is generally added in an amount of at least 10 percent by weight and preferably between about 50 to 60 percent by weight of the combined slurry mixture.

The following examples are provided to illustrate the invention in accordance with the principles of this invention but are not to be considered as limiting the invention in any way except as indicated by the appended claims.

In the Examples which follow that are directed to unsaturated hydrocarbon oxidation employing the instant thallium promoted $VO(PO_3)_2$ catalyst, the reactions were run in a 5/8 inch inside diameter stainless steel U-tube reactor which was immersed in a fluidized sand bath for maintaining the temperature of reaction. The lower half of the U-tube reactor was filled with catalyst having an 8–16 mesh (Standard Sieve). The thallium promoted $VO(PO_3)_2$ (precursor) catalyst was activated or conditioned in a stream of air with 1 volume percent of unsaturated hydrocarbon at a desired temperature for several hours at an appropriate apparent contact time over the catalyst. Following activation the temperature is decreased to the desired oxidation reaction temperature and the flow of hydrocarbon-air mixture, with or without the addition of steam, adjusted to the desired apparent contact time of between 0.5 to 3.0 seconds. The gaseous effluent oxidation reaction products from the reactor were passed through a series of water traps to adsorb the maleic anhydride and other by-products such as small amounts of acetic and acrylic acids; the maleic anhydride being converted to maleic acid in the aqueous solution. The gaseous effluent from the U-tube reactor was analyzed by InfraRed (I.R.) and gas chromatography to determine the concentration of carbon dioxide, carbon monoxide and any unconverted hydrocarbon. The aqueous solution containing the maleic acid was analyzed by gas chromatography to determine maleic anhydride yield and selectivity. Percent conversion of hydrocarbon and percent selectivity to maleic anhydride are calculated in mole percent.

EXAMPLE 1

A thallium promoted vanadium(IV)bis(metaphosphate) catalyst was prepared as follows: 64.24 grams (0.400 moles) of vanadyl sulfate ($VOSO_4$) along with 3.0 grams (0.0066 moles) of thallic oxide ($Tl_2O_3$) was added to 175 ml. of acetic anhydride at ambient temperature of 26° C. and stirred. 58.76 grams (0.414 moles) of phosphorus pentoxide ($P_2O_5$) was slowly added to the solution with stirring forming a slurry and allowing the liberation of exothermic heat. Excess liquid was decanted from the slurry mixture and the resulting wet vanadyl sulfate-thallic oxide-phosphorus pentoxide product transferred to a furnace. The temperature of the furnace was increased at a rate of 1° C. per minute to a maximum of 450° C. and maintained for a period of 12 hours liberating reaction gases. After cooling the crystalline product was thoroughly washed with water to remove any soluble residue. After drying at 120° C. the product was calcined in air at 500° C. for three hours to give a thallium promoted $VO(PO_3)_2$ catalyst (precursor) having an intrinsic surface area of approximately 6.5 $m^2/g$. After calcination the catalyst (precursor) was broken up (8–16 Standard Sieve mesh size) for use, after activation and conditioning, in the oxidation 1-butene to maleic anhydride.

EXAMPLE 2

The procedure of Example 1 was repeated with the exception that 250 ml of acetic anhydride was employed at ambient temperature of 26° C. Excess liquid was decanted and the resulting slurry heated in the furnace at a rate of 1° C. per minute to a maximum of 425° C. and maintained for a period of 16 hours liberating reaction gases. After drying and calcination, as in Example 1 a thallium promoted $VO(PO_3)_2$ catalyst (precursor) having an intrinsic surface area of 12.5 $m^2/g$. resulted.

EXAMPLE 3

An $SiO_2$—$Al_2O_3$ supported thallium promoted $VO(PO_3)_2$ catalyst was prepared as follows: 64.24 grams (0.400 moles) of vanadyl sulfate, 3.0 grams (0.0066 moles) of thallic oxide along with 90.0 grams of $SiO_2$—$Al_2O_3$ was added to 250 ml of acetic anhydride. 58.76 grams of phosphorus pentoxide was slowly added with stirring. Excess liquid was decanted and the resulting mixture heated in a furnace at a rate of 1° C. per minute to a maximum of 450° C. and maintained for a period of 12 hours liberating the reaction gases. After cooling the product was washed with water to remove any soluble residue and dried at a temperature of 120° C. The dried product was calcined in air at 500° C. for 3 hours giving an SiO$_2$—Al$_2$O$_3$ supported thallium promoted VO(PO$_3$)$_2$ catalyst (precursor) with an intrinsic surface area of 25.9 m$^2$/g. on the support.

EXAMPLE 4

Example 1 was repeated with the exception that 250 ml of acetic anhydride and 9.12 grams (0.02 moles) of thallic oxide were employed. After drying and calcination a thallium promoted VO(PO$_3$)$_2$ catalyst (precursor) having an intrinsic surface area of 13.1 m$^2$/g. with a 1:10 thallium to vanadium molar ratio resulted.

EXAMPLE 5

A number of runs were made employing 30 ml of the thallium promoted vanadium(IV)bis(metaphosphate) catalyst of Example 2 loaded into the lower half of a U-tube reactor which was immersed in a fluidized sand bath. The catalyst (precursor) was activated in a stream of air, steam and 1 volume percent of 1-butene at 490° C. for 16 hours at an apparent contact time of approximately 3.0 seconds. Following conditioning (activation) of the catalyst the reaction temperature was decreased to the desired temperature and the apparent contact time adjusted to desired conditions. Results giving conversions and selectivities to maleic anhydride are shown in Table 1 below.

TABLE 1

| Run No. | Contact Time (sec.) | Temp. °C. | Mole % Steam | Mole %$^{(1)}$ Conversion | Mole %$^{(2)}$ Selectivity to Maleic Anhydride |
|---|---|---|---|---|---|
| 1 | 0.91 | 463 | 25.7 | 96 | 64.5 |
| 2 | 0.87 | 472 | 22.8 | 93 | 62.4 |
| 3 | 1.06 | 491 | 33.4 | 99 | 67.2 |

$^{(1)}$% conversion determined by gas chromatograph analyses of C$_4$ 4 effluent gas.
$^{(2)}$% selectivity to maleic anhydride determined by gas chromatograph.

EXAMPLE 6

The procedure of Example 5 was repeated employing 30 ml of the SiO$_2$—Al$_2$O$_3$ supported thallium promoted VO(PO$_3$)$_2$ catalyst (precursor) of Example 3. The catalyst (precursor) was activated in a stream of air, steam and 1 volume percent of 1,3-butadiene at 500° C. for 10 hours at an apparent contact time of 3.0 seconds. Following conditioning of the catalyst the reaction temperature was decreased to the desired temperature and the apparent contact time adjusted to desired conditions. Results giving conversions and selectivities to maleic anhydride are shown in Table 2 below.

TABLE 2

| Run No. | Contact Time (sec.) | Temp. °C. | Mole % Steam | Mole %$^{(1)}$ Conversion | Mole %$^{(2)}$ Selectivity to Maleic Anhydride |
|---|---|---|---|---|---|
| 1 | 1.50 | 400 | 20.5 | 97 | 66.5 |
| 2 | 1.00 | 425 | 22.6 | 96 | 65.4 |
| 3 | 0.75 | 450 | 18.0 | 99 | 67.0 |

$^{(1)}$% conversion determined by gas chromatograph analyses of C$_4$ in effluent gas.
$^{(2)}$% selectivity to maleic anhydride determined by gas chromatograph.

We claim:

1. A method for the preparation of a thallium promoted single phase crystalline vanadium(IV)bis(metaphosphate) hydrocarbon oxidation catalyst which comprises the steps of:
    forming a slurry of vanadyl sulfate, thallic oxide, acetic anhydride and phosphorus pentoxide with the liberation of exothermic heat;
    introducing said slurry into a heating zone and maintaining said zone at a temperature of at least about 325° C. for a period sufficient for the liberation of gases and forming a thallium-vanadium-phosphorus reaction product;
    cooling the reaction product and washing with water to essentially remove any soluble residue;
    drying the water washed product and calcining in air to obtain a thallium containing single phase crystalline vanadium(IV)bis(metaphosphate) catalyst.

2. A method according to claim 1 wherein the molar ratio of thallium to vanadium, employed in the form of thallic oxide and vanadyl sulfate, is in the range of from about 1:10 to 1:150.

3. A method according to claim 2 wherein the ratio is 1:90.

4. A method according to claim 1 wherein the vanadyl sulfate-thallic oxide-acetic anhydride-phosphorus pentoxide slurry is formed at ambient temperature.

5. A method according to claim 1 wherein at least stoichiometric quantities of vanadyl sulfate and phosphorus pentoxide are employed to form the slurry.

6. A method according to claim 1 wherein the amount of acetic anhydride employed is in the range of from about 1 to 4 moles per mole of the combined vanadyl sulfate, thallic oxide and phosphorus pentoxide employed.

7. A method according to claim 1 wherein the amount of acetic anhydride employed is from about 2 to 3 moles.

8. A method according to claim 1 wherein excess liquid is decanted from the slurry prior to introduction into the heating zone.

9. A method according to claim 1 wherein the slurry is reacted at a temperature of between about 400° C. and 460° C.

10. A method according to claim 1 wherein the thallium-vanadium-phosphorus reaction product is dried at a temperature of 120° C. and calcined in air at a temperature of at least 450° C.

11. A method according to claim 1 wherein the thallium promoted single phase crystalline vanadium(VI)bis(metaphosphate) catalyst is prepared in the presence of a suitable carrier or support.

12. A method according to claim 11 wherein the carrier or support material is added to the thallic oxide, vanadyl sulfate, acetic anhydride, phosphorus pentoxide slurry.

13. A method according to claim 12 wherein the carrier or support is an aluminosilicate.

14. A method according to claim 1 wherein the thallium containing single phase crystalline vanadium(VI)bis(metaphosphate) catalyst in the unsupported state has an intrinsic surface area of from about 5 to 25 m$^2$/g.

* * * * *